(12) United States Patent
Sicken et al.

(10) Patent No.: US 6,583,315 B2
(45) Date of Patent: Jun. 24, 2003

(54) PROCESS FOR PREPARING ETHANEBIS (ALKYLPHOSPHINIC) ACIDS

(75) Inventors: Martin Sicken, Köln (DE); Norbert Weferling, Hürth (DE); Hans-Peter Schmitz, Brühl (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/025,739

(22) Filed: Dec. 19, 2001

(65) Prior Publication Data

US 2003/0073865 A1 Apr. 17, 2003

(30) Foreign Application Priority Data

Dec. 23, 2000 (DE) ......................................... 100 65 051

(51) Int. Cl.$^7$ ................................................. C07F 9/30
(52) U.S. Cl. ....................................................... 562/20
(58) Field of Search ........................................ 562/8, 20

(56) References Cited

U.S. PATENT DOCUMENTS

| | | | |
|---|---|---|---|
| 2,731,458 A | * 1/1956 | Garwood et al. | ............... 562/8 |
| 2,957,931 A | 10/1960 | Hamilton et al. | |
| 3,579,576 A | * 5/1971 | Angstadt | .................... 562/816 |
| 3,962,194 A | 6/1976 | Bollert et al. | |
| 4,001,352 A | 1/1977 | Kleiner et al. | |
| 4,613,674 A | * 9/1986 | Tsolis et al. | ................. 558/161 |
| 4,670,193 A | * 6/1987 | Thottathil | ....................... 562/8 |
| 4,762,649 A | 8/1988 | Coleman | |
| 5,780,534 A | 7/1998 | Kleiner et al. | |
| 6,013,707 A | 1/2000 | Kleiner et al. | |
| 6,278,012 B1 | * 8/2001 | Horold et al. | ............... 558/110 |
| 6,388,125 B1 | * 5/2002 | Schmitz et al. | ................. 562/8 |

FOREIGN PATENT DOCUMENTS

| | | |
|---|---|---|
| DE | 2 158 765 | 5/1973 |
| DE | 2 236 037 | 2/1974 |
| DE | 2 302 523 | 8/1974 |
| EP | 0 699 708 | 3/1996 |

OTHER PUBLICATIONS

CA:105:226805 abst of Zh. Obshch. Khim. 56(4) pp. 773–781 by Nifant'ev et al 1986.*
English abstract for DE 2158765, May 30, 1973.
U.S. patent application, Ser. No. 10/025,712, filed Dec. 19, 2001, Sicken, et al.
U.S. patent application, Ser. No. 10/046,107, filed Dec. 19, 2001, Sicken, et al.

S.M. Shner, et al., "Reactions of BIS–2–Chloroethyl Hydrogen Phosphite and Its Derivatives", J. Gen. Chem., USSR, 37, (1967), p. 390–392.
K. Moedritzer, et al., "Synthesis and Properties of Mono– and Poly– Methylene–Diphosphonic Acids and Esters", J. Inorg. Nucl. Chem., 1961, vol. 22, p. 297–304.
Claibourne E. Griffin, et al., "Phosphonic Acids and Esters. I. Radical Initiated Addition of Phosphorous Acid to Olefins", 24, (1959), p. 2049–2051.
Przemyslaw Mastalerz, "Synthesis of some ethylene—(P, P'–Dialkyl)–Diphosphinic acids as new potential antimetabolites of succinic acid", Roczniki Chem., Ann. Soc. Chem. Polonorum, 38, 61, (1964), p. 61–65.

* cited by examiner

Primary Examiner—Jean F. Vollano
(74) Attorney, Agent, or Firm—Anthony A. Bisulca

(57) ABSTRACT

The invention relates to a process for preparing ethanebis (alkylphosphinic) acids by
a) reacting elemental yellow phosphorus with alkyl halides in the presence of alkali metal hydroxide or of alkaline earth metal hydroxide to give a mixture whose main constituents are the alkali metal salts and/or alkaline earth metal salts of alkylphosphonous, phosphorous, and hypophosphorous acid,
b) liberating alkylphosphonous, phosphorous, and hypophosphorous acid by adding mineral acids, and also at the same time precipitating the alkali metal ions and, respectively, alkaline earth metal ions in the form of their salt of the mineral acids, and then
c) esterifying the alkylphosphonous acid from the mixture of the alkylphosphonous, phosphorous, and hypophosphorous acid,
d) isolating the ester of alkylphosphonous acid from the mixture and hydrolyzing the same to give alkylphosphonous acid, and
e) preparing, from the alkylphosphonous acid, the corresponding ethanebis(alkylphosphinic) acid of the general formula (I) where $R_1$ and $R_2$ may be identical or different and are hydrogen, a carboxy group, a carboxylic acid derivative, an unsubstituted or substituted alkyl group having from 1 to 10 carbon atoms, phenyl, benzyl, or alkyl-substituted aromatics, and $R_3$ and $R_4$ are identical or different and are an unsubstituted or substituted alkyl group having from 2 to 20 carbon atoms, by free-radical-initiated reaction with alkynes, and also to the use of the ethanebis(alkylphosphinic) acids prepared by this process as starting material for preparing flame retardants and precursors for the synthesis of other phosphorus-containing compounds.

27 Claims, No Drawings

PROCESS FOR PREPARING ETHANEBIS (ALKYLPHOSPHINIC) ACIDS

BACKGROUND OF THE INVENTION

The present invention relates to a process for preparing ethanebis(alkylphosphinic) acids, and also to the use of the products prepared by this process.

Phosphinic acids and salts of these may be prepared by a variety of methods, and have been described widely within the literature.

Organic phosphinic acids, and their salts and esters are known flame retardants. For example, EP 0 699 708 A1 describes flame-retardant polyester molding compositions, these being rendered flame-retardant by adding the calcium or aluminum salts of phosphinic or diphosphinic acids. The abovementioned salts are obtained by reacting the corresponding phosphonic acids with calcium hydroxide or aluminum hydroxide.

Due to their high phosphorus content and especially their bidentate. nature, the diphosphinic acids are described as highly effective reactive flame retardants for polyesters, e.g. for textile applications. This also applies to ethanebis (methylphosphinic) acid, specifically in the form of its glycol ester (DE 22 36 037 A1).

The preparation of these diphosphinic acids is technically complicated and takes place by an Arbuzov reaction of phosphonous diesters with alkyl dihalides [P. Mastalerz, Rocziniki Chem 38 (1964), pp. 61–64], followed by cleavage of the esters. The phosphonous diesters used are prepared from the corresponding phosphonous dihalides by reaction with alcohols.

Another way of preparing ethanediphosphonic acids is proposed in DE 23 02 523 A1 by reacting alkylphosphonous esters with acetylene and then cleaving the diester with HCl, with formation of alkyl chlorides. Here again, the alkylphosphonous esters used are prepared from the corresponding phosphonous dihalides by hydrolysis and reaction with alcohols.

The abovementioned process has the disadvantage of first requiring inconvenient preparation of the appropriate organic phosphorus compounds. This applies particularly to the esters of alkylphosphonous acids, which in turn are prepared from the corresponding phosphonous dihalides, such as methyldichlorophosphine. Methyldichlorophosphine is prepared by complicated syntheses (Houben-Weyl, Vol. 12/1, pp. 306). In addition, there are byproducts formed which, like some of the above mentioned starting materials, are toxic, or ignite spontaneously, and/or are corrosive, i.e. are highly undesirable.

Another disadvantage is that all of the processes described above for preparing ethanebis(alkylphosphinic) acids have the technically difficult cleavage of the corresponding esters as a final step.

SUMMARY OF THE INVENTION

The object on which the invention is based is therefore to provide a process which can prepare ethanebis (alkylphosphinic) acids and avoids the abovementioned disadvantages, and can be carried out in a particularly simple and economic manner, and which gives a high yield of single products. This process should also be clearly superior to the known processes in its effect on the environment. The starting material for the process of the invention is elemental yellow phosphorus, which is easily obtainable, and the process cannot require the complicated cleavage of diphosphinic esters.

This object is achieved by a process for preparing ethanebis(alkylphosphinic) acids by a) reacting elemental yellow phosphorus with alkyl halides in the presence of alkali metal hydroxide or of alkaline earth metal hydroxide to give a mixture whose main constituents are the alkali metal salts and/or alkaline earth metal salts of alkylphosphonous, phosphorous, and hypophosphordus acid, b) liberating alkylphosphonous, phosphorous, and hypophosphorous acid by adding mineral acids, and also at the same time precipitating the alkali metal ions and, respectively, alkaline earth metal ions in the form of their salt of the mineral acids, and then c) esterifying the alkylphosphonous acid from the mixture of the alkylphosphonous, phosphorous, and hypophosphorous acid, d) isolating the ester of alkylphosphonous acid from the mixture and hydrolyzing the same to give alkylphosphonous acid, and e) preparing, from the alkylphosphonous acid, the corresponding ethanebis(alkylphosphinic) acid of the general formula (I)

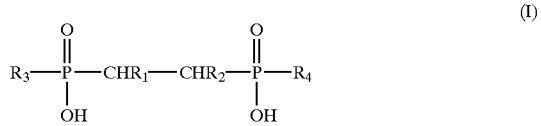

where $R_1$ and $R_2$ may be identical or different and are hydrogen, a carboxy group, a carboxylic acid derivative, an unsubstituted or substituted alkyl group having from 1 to 10 carbon atoms, phenyl, benzyl, or alkyl-substituted aromatics, and $R_3$ and $R_4$ are identical or different and are an unsubstituted or substituted alkyl group having from 2 to 20 carbon atoms, by free-radical-initiated reaction with alkynes.

Compared with the processes known hitherto, the process of the invention has considerable advantages since it, inter alia, avoids the use of phosphines or phosphonous dihalides as starting materials, produces no halogenated organic byproducts, involves no complicated cleavage of phosphinic esters, and also has a positive balance in relation to product distribution. The process is highly effective and economic to carry out.

DETAILED DESCRIPTION OF THE INVENTION

The alkyl halides used are preferably methyl chloride or methyl bromide.

The reaction in step a) is preferably carried out in a two-phase system of aqueous alkali metal hydroxide or alkaline earth metal hydroxide or a mixture of these, and an organic solvent.

The organic solvents preferably used in step a) are straight-chain or branched alkanes, alkyl-substituted aromatic solvents, or water-immiscible or only partially water-miscible alcohols or ethers, alone or in combination with one another.

An organic solvent whose use is particularly preferred is toluene, alone or combined with alcohols.

The reaction is preferably carried out in the presence of a phase-transfer catalyst.

The phase-transfer catalyst is preferably a tetraalkylphosphonium halide, triphenylalkylphosphonium halide, or tetraorganylammonium halide.

The temperature during the reaction in step a) is preferably from −20 to +60° C.

The temperature is particularly preferably from −10 to +30° C.

The reaction is preferably carried out at a pressure of from 0 to 10 bar.

The method of carrying out step a) of the process of the invention is preferably that the yellow phosphorus is suspended in a solvent or solvent mixture and then reacted with alkyl halide and a compound of the formula MOH or M'(OH)$_2$, or a mixture of these, where M is an alkali metal and M' is an alkaline earth metal.

It is preferable for the yellow phosphorus and the alkyl halide to be reacted with one another in a molar ratio of from 1:1 to 1:3, the molar ratio of yellow phosphorus to the compound of the formula MOH or M'(OH)$_2$ being from 1:1 to 1:5.

Step b) preferably comprises neutralization by addition of a mineral acid.

Step b) preferably comprises neutralization by addition of hydrochloric acid.

The alkali metal salt of the mineral acid and, respectively, alkaline earth metal salt of the mineral acid is preferably precipitated by exchanging the solvent, water, for the alcohol to be used in reaction step c).

The small amounts of phosphines obtained in step b) are preferably removed by oxidation.

The oxidant used preferably comprises hydrogen peroxide.

In step c) the alkylphosphonous acid is preferably esterified directly with a linear or branched alcohol of the general formula R—OH, where R is a linear or branched alkyl radical having from 1 to 10 carbon atoms.

The alcohol is preferably isobutanol, n-butanol, and/or 2-ethylhexanol.

The alkali metal salt of the mineral acid, or alkaline earth metal salt of the mineral acid, precipitated in step b) is preferably filtered off prior to the esterification process.

One way of esterifying the phosphonous acid to give the corresponding monoester is reaction with higher-boiling alcohols, the water formed being removed by azeotropic distillation.

The alkylphosphonous acid used is preferably methanephosphonous acid.

In step d) the ester of the alkylphosphonous acid is preferably removed by distillation.

In step d) the distilled ester of the alkylphosphonous acid is preferably hydrolyzed with water, and the resultant alcohol is preferably distilled off.

In step e), the alkylphosphonous acid is preferably reacted with an alkyne in the presence of a free-radical initiator.

The free-radical initiators used preferably comprise azo compounds.

The azo compounds are preferably cationic and/or non-cationic azo compounds.

The cationic azo compounds used preferably comprise 2,2'-azobis(2-amidinopropane) dihydrochloride or 2,2'-azobis(N,N'-dimethyleneisobutyramidine) dihydrochloride.

The non-cationic azo compounds used preferably comprise azobis(isobutyronitrile), 4,4'-azobis(4-cyanopentanoic acid), or 2,2'-azobis(2-methylbutyronitrile).

The free-radical initiators used preferably comprise peroxidic inorganic and/or peroxidic organic free-radical initiators.

The peroxidic inorganic free-radical initiators used preferably comprise hydrogen peroxide, ammonium peroxodisulfate, and/or potassium peroxodisulfate.

The peroxidic organic free-radical initiators used preferably comprise dibenzoyl peroxide, di-tert-butyl peroxide, and/or peracetic acid.

A wide selection of suitable free-radical initiators can be found by way of example in Houben-Weyl, Supplementary volume 20, in the chapter "Polymerisation durch radikalische Initiierung" [Free-radical-initiated polymerization] on pages 15–74.

The free-radical initiators are preferably metered in continuously during the reaction.

The free-radical initiators metered in continuously during the reaction are preferably in the form of a solution in the alkyne.

The free-radical initiators metered in continuously during the reaction are preferably in the form of a solution in the solvent used.

To prepare the ethanebis(alkylphosphinic) acids, alkylphosphonous acid obtained after the hydrolysis in step d) is reacted, in the presence of a free-radical initiator, with alkynes of the general formula (II)

$$R_1-C\equiv C-R_2 \qquad (II)$$

where $R_1$ and $R_2$ are identical or different and are hydrogen, a carboxy group, a carboxylic acid derivative, an unsubstituted or substituted alkyl group having from 1 to 10 carbon atoms, phenyl, benzyl, or alkyl-substituted aromatics.

The alkynes used may be either the unsubstituted alkyne where $R_1$ and $R_2$=H in formula (II), singly substituted derivatives where $R_1$=H and $R_2 \neq$H in formula (II), or else doubly substituted alkynes where $R_1$ and $R_2 \neq$H in formula (II).

Examples of these alkynes are ethyne, phenylacetylene, diphenylacetylene, propyne, 1-butyne, 2-butyne, 1-phenylbutyne, 1-pentyne, 2-pentyne, 1-phenyl-1-pentyne, 1-hexyne, 2-hexyne, 3-hexyne, 1-phenyl-1-hexyne, 1-heptyne, 1-octyne, 4-octyne, 1-nonyne, 1-decyne, 1-dodecyne, the alkynols propargyl alcohol, 1-butyn-3-ol, 2-butyn-1-ol, 2-butyne-1,4-diol, 1-pentyn-3-ol, 2-pentyn-1-ol, 4-pentyn-1-ol, 4-pentyn-2-ol, 3-hexyn-1-ol, 5-hexyn-1-ol, 3-hexyne-2,5-diol, 2-octyn-1-ol, 1-octyn-3-ol, 3-nonyn-1-ol, 3-decyn-1-ol, and also propargyl chloride, propargyl bromide, propargylamine, propiolic acid, methyl propiolate, ethyl propiolate, 2-butynoic acid, ethyl 2-butynoate, 4-pentynoic acid, 5-hexynonitrile, 2-octynoic acid, methyl 2-octynoate, methyl 2-nonynoate, acetylenedicarboxylic acid, diethyl acetylenedicarboxylate, and dimethyl acetylenedicarboxylate.

Preferred alkynes are the 1-alkynes, propargyl alcohol, butynediol, propiolic acid, and acetylenedicarboxylic acid derivatives. Particular preference is given to the use of ethyne(acetylene).

The reaction preferably takes place at a temperature of from 40 to 200° C.

The reaction particularly preferably takes place at a temperature of from 70 to 130° C.

The reaction preferably takes place in the presence of a solvent.

The reaction preferably takes place in acetic acid as solvent.

The reaction preferably takes place by introducing gaseous acetylene (ethyne) at atmospheric pressure.

The reaction preferably takes place at superatmospheric pressure.

The manner of conducting the process is preferably such that after partial conversion the precipitating ethanebis(alkylphosphinic) acid is filtered off, and further alkyne is added after replacing the alkylphosphonous acid consumed.

The present invention also provides a process in which yellow phosphorus is reacted with methyl chloride in the presence of sodium hydroxide solution and of the phase-transfer catalyst tributylhexadecylphosphonium bromide, to give the sodium salt of the methylphosphonous acid, and the free acid is liberated from this by adding hydrochloric acid, and is esterified with 2-ethylhexanol in the mixture, the ester is isolated by distillation and hydrolyzed, and the resultant pure methanephosphonous acid is reacted with acetylene (ethyne) in the presence of a cationic or non-cationic free-radical initiator or in the presence of a peroxidic free-radical initiator, to give ethanebis(methylphosphinic) acid.

The present invention also provides a process in which yellow phosphorus is reacted with methyl chloride in the presence of sodium hydroxide solution and of the phase-transfer catalyst tributylhexadecylphosphonium bromide, to give the sodium salt of the methylphosphonous acid, and the free acid is liberated from this by adding hydrochloric acid, and is esterified with 2-ethylhexanol in the mixture, the ester is isolated by distillation and hydrolyzed, and the resultant pure methanephosphonous acid is reacted with acetylene (ethyne) in the presence of a cationic or non-cationic free-radical initiator or in the presence of a peroxidic free-radical initiator in acetic acid, to give ethanebis(methylphosphinic) acid, and this is continuously removed from the reaction mixture by a circulating filter system, and the methanephosphonous acid consumed is likewise continuously replaced by fresh acid.

The desired diphosphinic acids are obtained with high selectivity and high purity.

Either alkylphosphonous acids or the alkynes may be used in excess, since the reaction partners always react in a molar ratio of 2 to 1 (alkylphosphonous acid to alkyne).

The invention also provides the use of the ethanebis(alkylphosphinic) acids prepared by the process of the invention as starting materials for preparing flame retardants for polymers.

The invention further provides the use of the ethanebis(alkylphosphinic) acids prepared by the process of the invention as starting materials for preparing flame retardants for thermoplastic polymers, such as polyethylene terephthalate, polybutylene terephthalate, or polyamide.

The invention also provides the use of the ethanebis(alkylphosphinic) acids prepared by the process of the invention as starting material for preparing flame retardants for thermoset resins, such as unsaturated polyester resins, epoxy resins, polyurethanes, or acrylates.

Finally, the invention also provides the use of the ethanebis(alkylphosphinic) acids prepared by the process of the invention as precursors for the chemical synthesis of other phosphorus-containing compounds.

EXAMPLES

The example below illustrates the invention:

Example 1: Ethanebis(methylphosphinic) acid a) Reaction of yellow phosphorus with methyl chloride

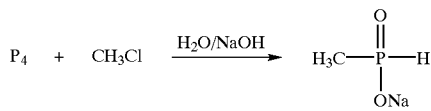

A solution of 26.1 (0.05 mol) of tributylhexadecylphosphonium bromide in 1000 ml of toluene was charged to a 5l stainless steel pressure reactor and preheated to 600° C. 62 g (2 mol) of yellow phosphorus were added, followed by cooling to −100° C. with vigorous stirring, and 202 g (4 mol) of methyl chloride were then condensed into the mixture. 400 g of 50% strength aqueous sodium hydroxide solution were then metered in within a period of 2 hours, keeping the temperature at −10° C. 400 g of water were added within a period of one hour, and then stirring was continued for a further hour, the mixture was warmed to room temperature, and then the reactor was depressurized via a flare. This gave two homogeneous liquid phases, which were separated and analyzed.

The aqueous phase (weight: 920 g) comprised 65.6 mol% of methylphosphonous acid, 14.9 mol% of phosphorous acid, and 13.7 mol% of hypophosphorous acid, and 2.8 mol% of dimethylphosphinic acid in the form if its sodium salt, and also 3 mol% of dimethyldiphosphine.

b) Conversion of the Na salts into the acids and NaCl separation:

The solution was treated progressively with 60 g of 5% strength aqueous hydrogen peroxide solution, 240 g of 36% strength hydrochloric acid, and 400 g of 2-ethylhexanol. After removal of the resultant water by distillation on a water separator, the precipitated sodium chloride was filtered off and washed with 100 g of 2-ethylhexanol.

c) Esterification of methanephosphonous acid with 2-ethylhexanol in the reaction mixture:

The ethylhexanol solutions from example 1 were combined and heated at about 120° C. for about 6 h in the water separator under slightly reduced pressure.

d) Isolation of methanephosphonous acid:

The esterified reaction mixture was then freed from excess ethylhexanol by distillation and subjected to vacuum distillation. 220 g of the 2-ethylhexyl ester of methanephosphonous acid distilled at a head temperature of 75° C. and a pressure of 0.3 mm. The product is a clear colorless liquid with purity above 99%, corresponding to a yield of 58%, based on the yellow phosphorus used. Analyses: 16.0% phosphorus (theory: 16.2%); $^{31}$P NMR: Dublett at 34 ppm (diastereomeric pair). The ester is then heated for 2 hours at reflux with 50 g of water, and then freed from resultant alcohol-water mixture under the vacuum provided by a water jet.

e) Reaction with acetylene (ethyne)

A solution of 93 g of methanephosphonous acid from d) in 200 g of glacial acetic acid is heated to about 90° C. in a 1 l 5-necked flask equipped with gas inlet frit, thermometer, stirrer, reflux condenser, and initiator metering. A solution of 14 g (5 mol%) of ammonium peroxodisulfate in 30 g of water is metered in over a period of 5 h, with vigorous stirring. At the same time, about 10 l/h of acetylene are conducted through the solution by way of the gas inlet frit, excess acetylene being passed to a flare. The reaction temperature here is held at from about 95 to 1 05° C. Once the acetylene had been removed by flushing with nitrogen, the mixture was cooled, whereupon ethanebis (methylphosphinic) acid precipitates. This is filtered off, washed twice, each time with 50 ml of acetic acid, and dried at 100° C. under the vacuum provided by a water jet. This gives about 78 g of ethanebis (methylphosphinic) acid in the form of colorless crystals with a melting point of 197° C. (70% of theory, based on the methanephosphonous acid used). The mother liquor comprises further final product and may be utilized for further reactions. Elemental analysis: P: calc. 33.3%, found 33.0%; $^{31}$P NMR spectrum (D$_2$O): δ=55 ppm (singlet); purity ($^{31}$P NMR): 99%.

What is claimed is:

1. A process for preparing ethanebis(alkylphosphinic) acids comprising the steps of:
   a) reacting elemental yellow phosphorus with alkyl halides in the presence of alkali metal hydroxide or of alkaline earth metal hydroxide to give a mixture whose main constituents are the alkali metal salts and/or alkaline earth metal salts of alkylphosphonous, phosphorous, and hypophosphorous acid,
   b) liberating alkyiphosphonous, phosphorous, and hypophosphorous acid by adding mineral acids, and also at the same time precipitating the alkali metal ions and, respectively, alkaline earth metal ions in the form of their salt of the mineral acids, and then
   c) esterifying the alkylphosphonous acid from the mixture of the alkylphosphonous, phosphorous, and hypophosphorous acid,
   d) isolating the ester of alkylphosphonous acid from the mixture and hydrolyzing the same to give alkylphosphonous acid, and
   e) preparing, from the alkylphosphonous acid, the corresponding ethanebis(alkylphosphinic) acid of the general formula (I)

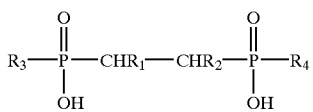

(I)

where R$_1$, and R$_2$ may be identical or different and are hydrogen, a carboxy group, an ester, an alcohol, an unsubstituted or substituted aikyl group having from 1 to 10 carbon atoms, phenyl, benzyl, or alkyl-substituted aromatics, and R$_3$ and R$_4$ are identical or different and are an unsubstituted or substituted alkyl group having from 2 to 20 carbon atoms. in the presense of at least one free radical initiator with alkynes.

2. The process as claimed in claim 1, wherein the reaction in step e) takes place at a temperature of from 70 to 130° C.

3. The process as claimed in claim 2, wherein the alkali metal salt of the mineral acid and, respectively, alkaline earth metal salt of the mineral acid is precipitated by exchanging the solvent for the alcohol to be used in reaction step c).

4. The process as claimed in claim 1, wherein, in step c), the alkylphosphonous acid is esterified directly with a linear or branched alcohol of the general formula R—OH, where R is a linear or branched alkyl radical having from 1 to 10 carbon atoms.

5. The process as claimed in claim 1, wherein the alcohol is isobutanol, n-butanol, and/or 2-ethylhexanol.

6. The process as claimed in claim 1, wherein the alkylphosphonous acid is methanephosphonous acid.

7. The process as claimed in claim 1, wherein, in step d), the ester of the alkylphosphonous acid is removed by distillation.

8. The process as daimed in claim 1, wherein, in step d), the isolated ester of alkyiphosphonous acid is hydrolyzed with water and the resultant alcohol is distilled off.

9. The process as claimed in claim 1, wherein the at least one free-radical initiator used comprise azo compounds.

10. The process as claimed in claim 9, wherein the azo compounds are selected from the group consisting of catlonic and non cationic azo compounds.

11. The process as claimed in claim 9, wherein the cationic azo compounds are selected from the group consisting of 2,2'-azobis(2-amidinopropane) dihydrochloride, and 2,2'-azobis(N,N'-dimethyleneisobutyramidine) dihydrochloride, and the non-catlonic azo compounds are selected from the group consisting of azobis (isobutyronitrile), 4,4'-azobis(4-cyanopentanoic acid) and 2,2'-azobis(2-methylbutyronitrile).

12. The process as claimed in claim 1, wherein the at least one free-radical initiator is selected from the group consisting of peroxidic inorganic and peroxidic organic free-radical initiators.

13. The process as claimed in claim 12, wherein the peroxidic inorganic free-radical initiators are selected from the group consisting of hydrogen peroxide, ammonium peroxodisulfate, and potassium peroxodisulfate, and the peroxidic organic free-radlcal initiators are selected from the group consisting of dibenzoyl peroxide, ditert-butyl peroxide, and peracetic acid.

14. The process as claimed in claim 1, wherein the at least one free-radical initiators is metered in continuously during the reaction.

15. The process as claimed in claim 14, wherein the at least one free-radical initiator metered in continuously during the reaction are in the form of a solution in the alkyne.

16. The process as claimed in claim 14, wherein the reaction takes place in the presence of a solvent and wherein the at least one free-radical inititor metered in continuously during the reaction are in the form of a solution in the solvent.

17. The process as daimed in claim 1, wherein the alkylphosphonous acid obtained after the hydrolysis in step d) is reacted, in the presence of a free-radical initiator, with alkynes of the general formula (II)

(II)

where R$_1$ and R$_2$ are identical or different and are hydrogen, a carboxy group, an ester, an alcohol, an unsubstituted or substituted alkyl group having from 1 to 10 carbon atoms, phenyl, benzyl, or alkyl-substituted aromatics.

18. The process as claimed in claim 17, wherein the alkynes selected from the group consisting of ethyne, phenylacetylene, diphenylacetylene, propyne, 1-butyne, 2-butyne, 1-phenylbutyne, 1-pentyne, 2-pentyne, 1-phenyl- 1-pentyne, 1-hexyne, 2-hexyne, 3hexyne, 1-phenyl-1-hexyne, 1-heptyne, 1-octyne, 4-octyne, 1-nonyne, 1-decyne, 11odecyne, the alkynols propargyl alcohol, 1-butyn-3-ol, 2-butyn-1-ol, 2-butyne-1,4-diol, 1-pentyn-3-ol, 2, 2-pentyn-1-ol, 4-pentyn-1-ol, 4-pentyn-2-ol, 3-hexyn-1-ol, 5-hexyn-1-ol, 3hexyne2,5diol, 2-octyn-1-ol, 1octyn-3ol, 3-nonyn-1-0l, 3-decyn-1-ol, propargyl chloride, propargyl bromide, propargylamine, propiolic acid, methyl proplolate, ethyl propiolate, 2-butynoic acid, ethyl 2-butynoate, 4-pentynoic acid, 5-hexynonitrile, 2-octynoic acid, methyl 2-octynoate, methyl 2-nonynoate, acetylenedicarboxylic acid, diethyl acetylenedicarboxylate, and dimethyl acetylenedicarboxylate.

19. The process as claimed in claim 17, wherein the alkynes are selected from the group consisting of 1alkynes, propargyl alcohol, butynediol, propiolic acid, and acetylenedlcarboxylic acid derivatives.

20. The process as claimed in claim 17, wherein the alkyne used is ethyne (acetylene).

21. The process as claimed in claim 1, wherein the reaction in step e) takes place at a temperature of from 40 to 200° C.

22. The process as claimed in claim 1, wherein the reaction takes place in the presence of a solvent.

23. The process of claim 22, wherein the solvent is water.

24. The process as claimed in claim 1, wherein the reaction takes place by introducing gaseous ethyne at atmospheric pressure.

25. The process as claimed in claim 1, wherein the reaction takes place at superatmospheric pressure.

26. The process as claimed in claim 1, wherein yellow phosphorous is reacted with methyl chloride in the presence of sodium hydroxide solution and of a phasetransfer catalyst which is tributylhexadecylphosphonium bromide, to give the sodium salt of the methylphdsphonous acid, and the free acid is liberated from this by adding hydrochloric acid, and the free acid of methylphosphonous acid is esterified with 2-ethylhexanol in the mixture, the ester is isolated by distillation and hydrolyzed, and the resultant pure methanephosphonous acid is reacted with acetylene in the presence of a cationic or noncationic azo free-radical initiator or in the presence of a peroxidic free-radical initiator, to give ethanebis(methylphosphinic) acid.

27. The process as claimed in claim 1, wherein yellow phosphorous is reacted with methyl chloride in the presence of sodium hydroxide solution and of the phase-transfer catalyst tributylhexadecylphosphonium bromide, to give the sodium salt of the methylphosphonous acid, and the free acid is liberated from this by adding hydrochloric acid, and is esterified with 2-ethylhexanol in the mixture, the ester is isolated by distillation and hydrolyzed, and the resultant pure methanephosphonous acid is reacted with acetylene in the presence of a cationic or non-cationic free-radical initiator or in the presence of a peroxidic free-radical initiator in acetic acid, to give ethanebis (methylphosphinic) acid, and this is continuously removed from the reaction mixture by a circulating filter system, and the methanephosphonous acid consumed is likewise continuously replaced by fresh acid.

* * * * *